(12) United States Patent
Arias et al.

(10) Patent No.: US 11,714,145 B2
(45) Date of Patent: Aug. 1, 2023

(54) SYSTEMS AND METHODS FOR FABRICATING CONFORMAL MAGNETIC RESONANCE IMAGING (MRI) RECEIVE COILS

(71) Applicant: The Regents of the University of California, Oakland, CA (US)

(72) Inventors: Ana Claudia Arias, Lafayette, CA (US); Karthik Gopalan, Berkeley, CA (US); Alla Mykhaylivna Zamarayeva, Berkeley, CA (US); Michael Zhi-Hong Liu, Duluth, GA (US); Shimon Michael Lustig, Moraga, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 17/530,863

(22) Filed: Nov. 19, 2021

(65) Prior Publication Data

US 2022/0075014 A1    Mar. 10, 2022

Related U.S. Application Data

(63) Continuation of application No. PCT/US2020/038077, filed on Jun. 17, 2020.
(Continued)

(51) Int. Cl.
*G01R 33/34* (2006.01)
*A61B 5/055* (2006.01)

(52) U.S. Cl.
CPC ........ *G01R 33/34007* (2013.01); *A61B 5/055* (2013.01)

(58) Field of Classification Search
CPC ............ G01R 33/34007; A61B 5/055
See application file for complete search history.

(56) References Cited

U.S. PATENT DOCUMENTS

2016/0334479 A1\* 11/2016 Poole ............ A61B 5/7203
2017/0293286 A1   10/2017 Aggarwal et al.
(Continued)

FOREIGN PATENT DOCUMENTS

JP    2016-511095 A    4/2016

OTHER PUBLICATIONS

Written Opinion of the International Searching Authority for PCT/US2020/038077 from the International Searching Authority, dated Sep. 28, 2020.
(Continued)

*Primary Examiner* — G. M. A Hyder
(74) *Attorney, Agent, or Firm* — Leydig, Voit & Mayer, Ltd.; Gerald T. Gray

(57) ABSTRACT

Methods for forming conformal magnetic resonance imaging (MRI) receive coil devices having at least one receive coil with at least one capacitor are provided and include providing a 3-dimensional (3D) mold structure matching a curvilinear shape of interest, and forming a receive coil pattern on an outer surface of the 3D mold structure. The forming of the receive coil pattern may include spraying and/or depositing a conductive material and a dielectric material on the outer surface of the mold structure to form the receive coil pattern. The forming a receive coil pattern may include forming the receive coil pattern on an outer surface of a flat substrate sheet, and vacuum forming an inner surface of the flat substrate sheet to the outer surface of the mold structure to form a shape-conforming substrate sheet. The shape-conforming substrate sheet may be removed from the mold and used in MRI studies.

20 Claims, 7 Drawing Sheets

Related U.S. Application Data

(60) Provisional application No. 62/862,293, filed on Jun. 17, 2019.

(56) References Cited

U.S. PATENT DOCUMENTS

2018/0097274 A1    4/2018   Chen
2018/0372817 A1   12/2018  Rahmat-Samii et al.

OTHER PUBLICATIONS

International Search Report for PCT/US2020/038077 from the International Searching Authority, dated Sep. 28, 2020.
Corea et al., "Screen-printed flexible MRI receive coils," Nature Communications 7:10839, DOI: 10.1038/ncomms10839, pub. Mar. 10, 2016.

* cited by examiner

Fig. 2A
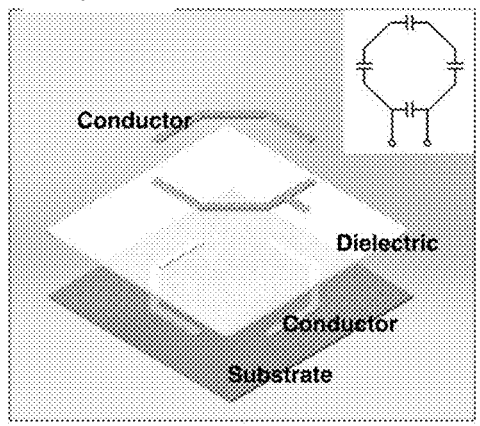
Fig. 2B
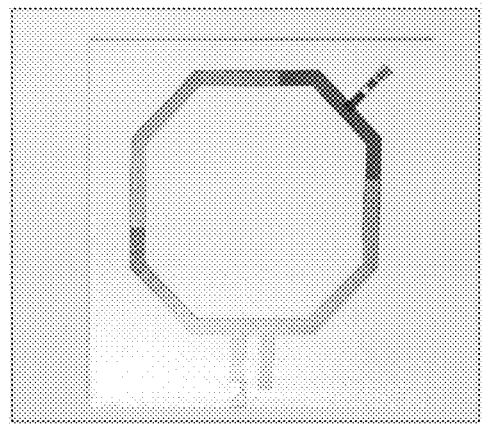
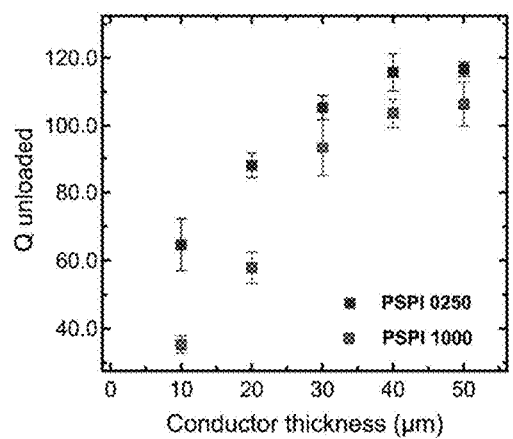
Fig. 2C
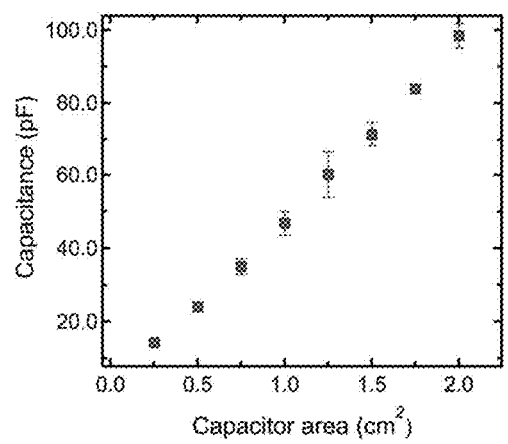
Fig. 2D

Fig. 3A
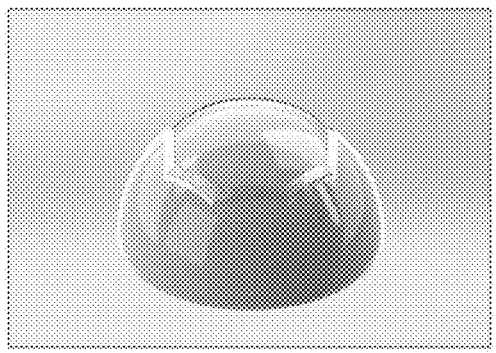
Fig. 3B
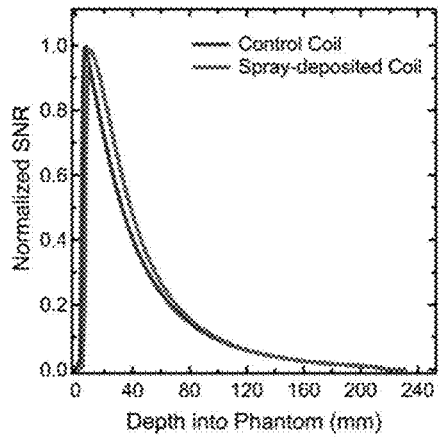
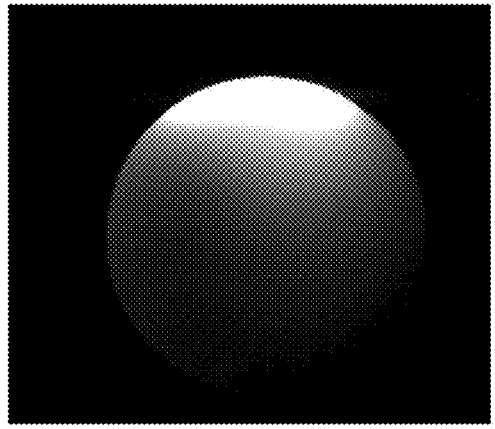
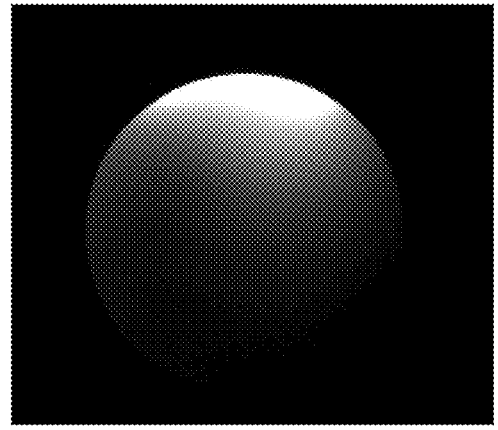
Fig. 3C Fig. 3D

Fig. 4A
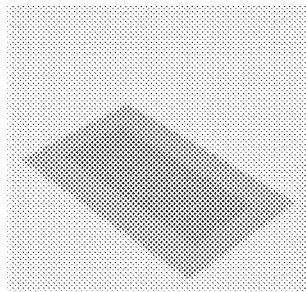
Fig. 4B
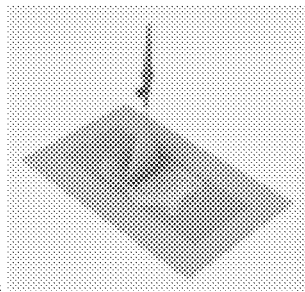
Fig. 4C
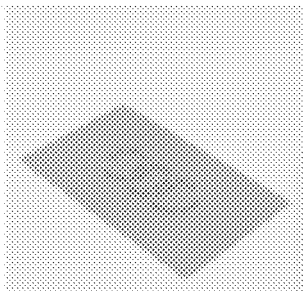
Fig. 4D
Fig. 4E
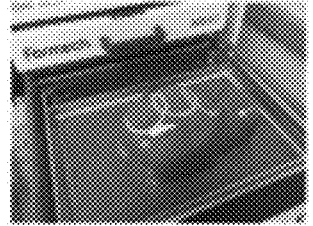
Fig. 4F
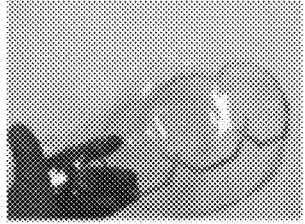
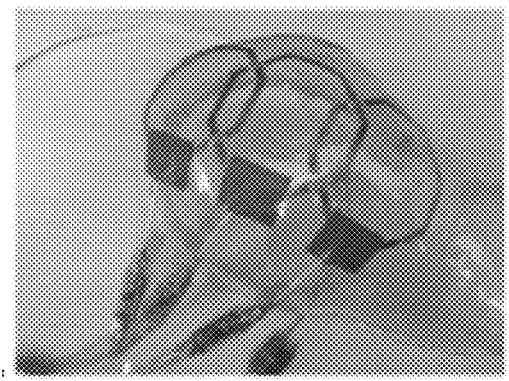
Fig. 4G

SYSTEMS AND METHODS FOR FABRICATING CONFORMAL MAGNETIC RESONANCE IMAGING (MRI) RECEIVE COILS

CROSS-REFERENCE TO RELATED APPLICATIONS

This patent application is a continuation of International Patent Application No. PCT/US2020/038077, filed on Jun. 17, 2020, which claims priority to U.S. Provisional Patent Application No. 62/862,293, filed Jun. 17, 2019, and which are both incorporated herein by reference in their entireties.

STATEMENT REGARDING FEDERALLY SPONSORED RESEARCH AND DEVELOPMENT

This invention was made with Government support under Grant Number EB015628 awarded by the National Institutes of Health. The Government has certain rights in this invention.

BACKGROUND

In Magnetic Resonance Imaging (MRI), very small signals are created via excitation of hydrogen protons in the bore of an MRI machine. These signals are picked up on receive coils adjacent to the patient inside the machine and processed to yield an image. The higher the signal-to-noise ratio (SNR) the receive coils can produce, the faster the scan time can be and the higher the quality of images that can be produced. MRI receive coil arrays provide a better signal-to-noise-ratio and field of view over standard single receive coils. However, this gain is lost when the surface coil array is at an improper distance from the patient.

Design and positioning of receive coils are one of the key factors determining SNR of the MR images. Particularly, placing receive coils in the close proximity to the body has been shown to significantly improve image quality. Commercial coils used in current clinical practice are not adapted to optimally fit every patient's anatomy; most MRI receive coils today have a rigid or semi-rigid structure and are one-size-fits-all, whereas patients come in a variety of sizes and shapes. A substantial gap between receive coils and the body often results in practice, which is detrimental to SNR. Additionally, further development of the next generation therapeutic approaches, such as MRI guided surgeries, relies on the ability to conduct multiple, often time-consuming, procedures on the same patient. This requires addressing additional issues associated with utilization of conventional coils, such as restriction of motion and the ability to position on a patient reproducibly.

There is therefore a need for MRI receive coil devices that provide increased SNR, and which provide improved patient conformity. There is also a need for cost-effective fabrication processes for forming such receive coil devices.

SUMMARY

The present disclosure provides conformal MRI receive coil devices, including conformal MRI receive coils arrays and method for manufacturing the same.

According to various embodiments, a process of fabricating patient-specific MRI receive coils includes scanning a body part or portion of interest of a patient using a structure sensor to determine the structure of the portion or body part of interest, 3-dimensional (3D) printing a custom substrate or mold conforming to the portion or body part of interest, and forming receive coil elements on the custom substrate or mold.

In an embodiment, a method of making a shape-conforming magnetic resonance imaging (MRI) receive coil device is provided. The method includes providing a 3-dimensional (3D) mold structure matching a curvilinear shape of interest, e.g., a portion or body part of a patient, and forming a receive coil pattern on an outer surface of the 3D mold structure.

In an embodiment, the 3D mold is thin and includes an inner surface and an outer surface, both conforming to the portion or body part of interest so that the mold itself is form-fitting to the portion or body part of interest. Forming the receive coil elements includes, in one embodiment, spray-depositing or spray painting coil components onto the outer surface of the mold using solution processed electronic materials. In this embodiment, the 3D mold acts as a substrate and comprises an MRI transparent material, such as a cyanide ester resin. When the receive coil elements have been formed on the substrate, the mold/substrate (with coils) may be applied to or attached to the portion or body part of interest of the patient for use in MRI imaging of the portion or body part of interest.

In another embodiment, the 3D mold has an outer surface that conforms to the portion or body part of interest, and may be thin or may be thick and solid. Receive coil elements are formed on a planar substrate sheet, e.g., by deposition and/or printing conductive materials in a coil pattern, and the planar sheet (with coils) is then heated and vacuum formed on the 3D mold, specifically on the outer surface of the 3D mold. In this embodiment, the planar substrate sheet (with coils) may be removed from the mold and may be applied to or attached to the portion or body part of interest of the patient for use in MRI of the portion or body part of interest. In another embodiment, a sheet may be vacuum sealed to an inside surface of the mold, e.g., a thin shell mold structure. In some embodiments, holes may be provided to assist with drawing plastic material into an internal cavity. In some embodiments, the receive coil pattern formed on the planar substrate may be pre-distorted, such that uniformly patterned coils are formed after the vacuum forming. In some embodiments, an isotropic, electroless metal plating is performed to fill in cracks in the conductive material of the coil elements that may have formed due to deformation during vacuum forming.

According to yet another embodiment, a flexible magnetic resonance imaging (MRI) receive coil device is provided, which is formed according to any of the methods herein.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 1A shows scanning of a patient's body part of interest (e.g., neck); FIG. 1B shows printing of a custom substrate for the body part of interest; FIG. 1C shows spray-depositing coil components onto custom-printed 3D substrates using solution processed electronic materials.

FIG. 2A and FIG. 2B show a schematic of the coil components, and a photograph of the full coil spray deposited onto a 2D substrate, respectively, according to an embodiment.

FIG. 2C shows performance of coils with different thickness of conductors, for two grades of Novacentrix silver inks—PSPI 1000 and PSPI 0250, according to embodiments.

FIG. 2D shows capacitance values for different areas of electrodes (controlled by changing the length of the top conductor trace), according to embodiments.

FIG. 3A shows a fully functional coil deposited onto a 3D spherical substrate, according to an embodiment.

FIG. 3B shows a comparison of the SNR of the two coils, evaluated using a spherical phantom.

FIGS. 3C and 3D show axial slices of the phantom obtained with spray-deposited and conventional coils, respectively.

FIG. 4A shows an example of polycarbonate masked with Kapton tap.

FIG. 4B shows a conductive material spray coated onto the substrate using an airbrush.

FIG. 4C shows the patterned substrate with the Kapton mask removed.

FIG. 4D and FIG. 4E show the sheet formed over a 3D printed head model.

FIG. 4F shows traces electroless plated with copper.

FIG. 4G shows rigid capacitors and Q-spoiling circuits attached with conductive epoxy.

DETAILED DESCRIPTION

The following detailed description is exemplary in nature and is not intended to limit the invention or the application and uses of the invention. Furthermore, there is no intention to be bound by any expressed or implied theory presented in the following detailed description or the appended drawings.

According to various embodiments, processes for fabricating patient-specific MRI receive coils are provided.

Custom, 3D Sprayed MRI Receive Coil Devices

Figure 1A:
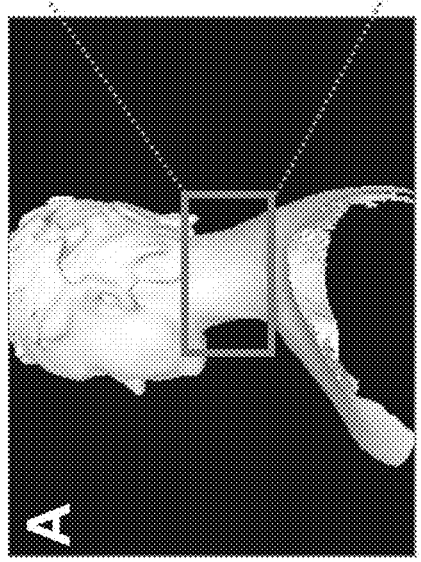
FIG. 1A, FIG. 1B and FIG. 1C show schematics of a fabrication flow for fabricating patient-specific MRI receive coils, according to an embodiment.
Figure 1B:
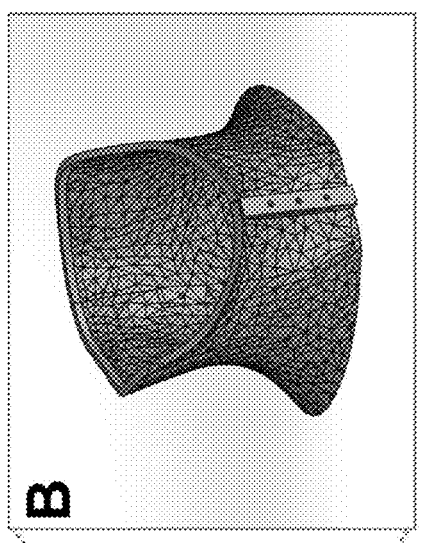
Figure 1C:
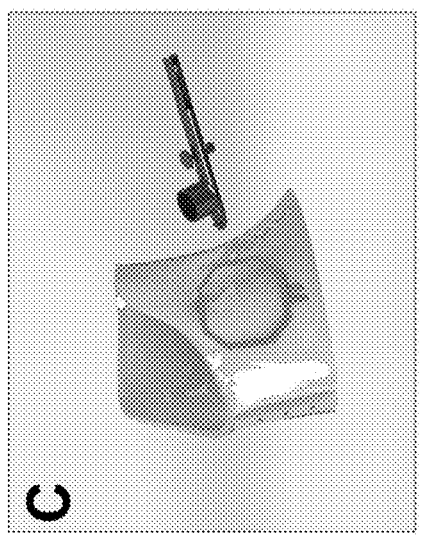

In an embodiment, a process includes scanning a body part of interest of the patient using commercially available structure sensor as shown in FIG. 1A, 3D printing a custom substrate for the body part of interest as shown in FIG. 1B and spray-depositing coil components onto custom printed 3D substrates using solution processed electronic materials as shown in FIG. 1C. This embodiment enables scalable and adaptable additive manufacturing of patient-specific MRI coils, advantageously opening a new pathway towards customization of MR imaging.

FIG. 2A and FIG. 2B show schematics of the coil components and a photograph of the full coil spray deposited onto a 2D substrate, respectively, according to an embodiment. A four-capacitor LC circuit is achieved by creating a pattern from two conductor layers with a dielectric in-between. Spray-deposition is used for fabricating coil components in an embodiment, as spray-deposition enables rapid deposition of a wide range of materials onto curvilinear surfaces. A carbon3D printing process and cyanide ester material are used to fabricate substrate in an embodiment. Cyanide ester is an MRI transparent, heat and flame resistant material, which makes it very useful as a high quality substrate for MRI receive coils. Polystyrene is used in an embodiment as the dielectric due to a low loss tangent factor, relatively high glass transition temperature of 100° C. (preferred for curing silver) and an ability to be solution-processed. The polystyrene to solvent (toluene) ratio may be adjusted to achieve an optimum spray-deposition process. Metallic ink, such as silver ink from Novacentrix, may be used as a conductor due to relatively low curing temperature (below glass transition temperature of polystyrene), simple handling, good rheological properties and, importantly, water-based solvent. Solvent used in the conductor ink should not have affinity to polystyrene—to avoid shorting between top and bottom conductor traces.

In studies, the optimum thickness of a sprayed conductor layer was found by evaluating the effect of silver trace thickness on the value of Q unloaded. FIG. 2C shows performance of coils with different thickness of conductor, for two grades of Novacentrix silver inks—PSPI 1000 and PSPI 0250. Q unloaded increases to the maximum value of about 120 for PSPI-0250 and about 110 for PSPI-1000, when the thickness of the conductor is increased to about 40 μm and about 50 μm, respectively. Increasing thickness beyond the indicated values does not contribute to a further increase in Q unloaded.

Controlling capacitance allows for effectively tuning the coil to the Larmor frequencies of MRI systems. FIG. 2D shows that varying the area of a capacitor from 0.25 $cm^2$ to 2 $cm^2$ results in capacitance values ranging from 13 pF to 102 pF, which is sufficient to reach specific frequencies of B64 MHz (1.5 T) and 127 MHz (3.0 T) used in MRI systems.

A fully functional coil deposited onto a 9 cm diameter 3D spherical substrate was fabricated as shown in FIG. 3A, and its performance was compared to a control coil of the same geometry, including metal copper traces with porcelain capacitors mounted onto a 2D flexible substrate. FIG. 3B shows a comparison of the SNR of the two coils, evaluated using a spherical phantom, evaluated using $NiCl_2$-doped saltwater 9 cm diameter spherical phantom. The control coil has the same geometry as the spray-deposited coil, and includes copper traces with low-loss porcelain capacitors mounted onto a 2D flexible substrate. FIGS. 3C and 3D show axial slices of the phantom obtained with spray-deposited and conventional coils, respectively. Due to improved conformability to the phantom, the spray-deposited coil provides greater coverage throughout and similar SNR, despite the lower performance characteristics of solution-processed materials. This illustrates an advantage of using custom printed MRI receive coils to image areas of the body with complex curvilinear geometries, such as a patient's neck. Furthermore, custom coils are constricting or form-fitting, which helps reduce or eliminate motion artifacts.

Custom, Vacuum-Formed MRI Receive Coil Devices

Vacuum forming is a scalable manufacturing technique wherein a planar thermoplastic sheet is heated, placed or pulled over a mold, and formed with an inward (toward the mold) vacuum force. In an embodiment, printing combined with vacuum forming is used to quickly fabricate highly conformal coils on complex 3D surfaces. Tuned 3D coil sets may manufactured automatically; utilizing 3D scanning, electromagnetic models, and mechanical simulation, tuned conformal circuits can be constructed without the need for human intervention. Embodiments herein may be used to rapidly manufacture extensive collections of coils of various shapes and sizes. In addition, fully custom coils may be manufactured for patients or volunteers who receive regular or periodic scans such as those in fMRI studies. This approach may also prove useful in MR-guided interventions by enabling access to the intervention area through strategically placed openings in the substrate.

In an embodiment, a receive coil device may be formed by forming a receive coil pattern on an outer surface of a flat substrate sheet such as a polycarbonate sheet or other material sheet, and then vacuum forming an inner surface of the flat substrate sheet to a surface of a mold structure matching a curvilinear shape of interest (e.g., body part) to form a shape-conforming substrate sheet. The shape-conforming sheet may be removed and used in an MRI study, e.g., applied to a patient for which the body part mold was designed.

As an example, a ⅛ inch sheet of polycarbonate is masked with Kapton tape, and coil geometries cut out of the tape, e.g., using a laser cutter such as a 25 watt CO laser cutter, as shown in FIG. 4A. The exposed area is cleaned, e.g., with isopropyl alcohol then rubbed with a 2M sodium hydroxide solution to etch the surface and promote adhesion. A conductive material, such as aqueous silver ink, is spray coated onto the substrate, e.g., using an airbrush such as a Badger 105 airbrush as shown in FIG. 4B. Heat is rapidly applied, e.g., using a heat gun or other heat source, to evaporate the solvent without sintering the conductive (e.g., silver) particles. The Kapton mask is removed as shown in FIG. 4C, and the sheet is formed over a 3D printed head model, e.g., using a vacuum source such as a Formech 300XQ vacuum forming machine, as shown in FIG. 4D and FIG. 4E.

Figure 5A:
FIG. 5A shows a printed silver on at substrate.
Figure 5B:
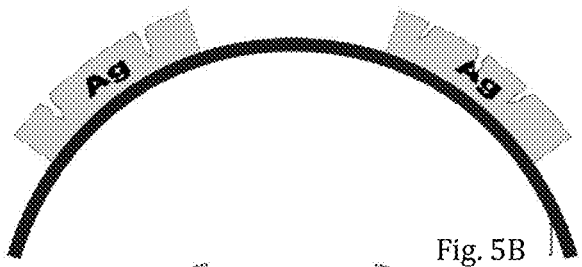
FIG. 5B shows micro-cracks formed after deformation.
Figure 5C:
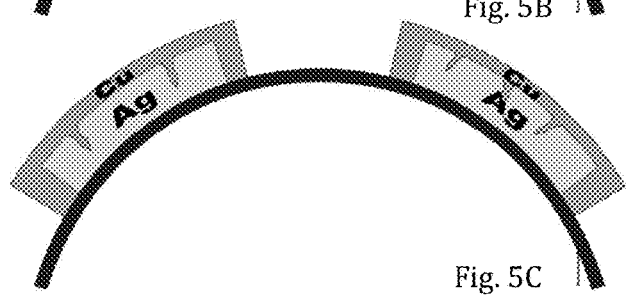
FIG. 5C shows isotropic, electroless copper plating filling in the cracks.
Figure 5D:
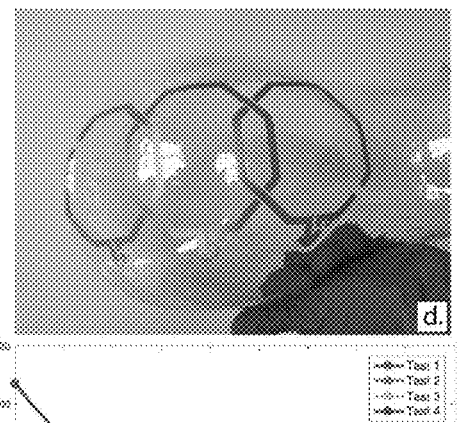
FIG. 5D shows conductors after electroless plating.
Figure 5E:
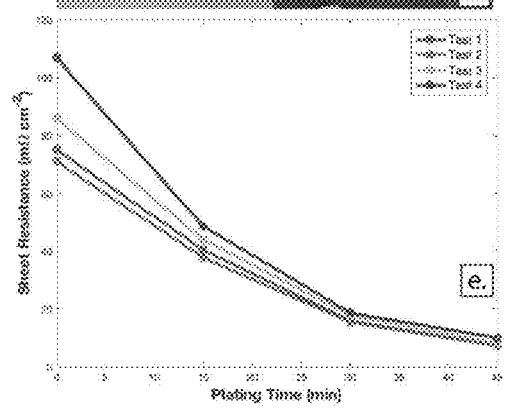
FIG. 5E shows a graph of sheet resistance vs. plating time for test strips were plated in a bath at 50° C.

The deformation during vacuum forming may introduce micro-cracks throughout the conductive (e.g., silver) traces, as shown in FIG. 5B, which may reduce conductivity. To combat the poor conductivity, the traces may be electroless plated, e.g., with copper using a solution consisting of $CuSO_4$, EDTA, NaOH, and formaldehyde, as shown in FIG. 4F and FIG. 5C. Electroless plating does not require an external voltage and the plating is isotropic. Next, rigid capacitors and Q-spoiling circuits may be attached, e.g., with conductive epoxy, as shown in FIG. 4G.

Figure 6:
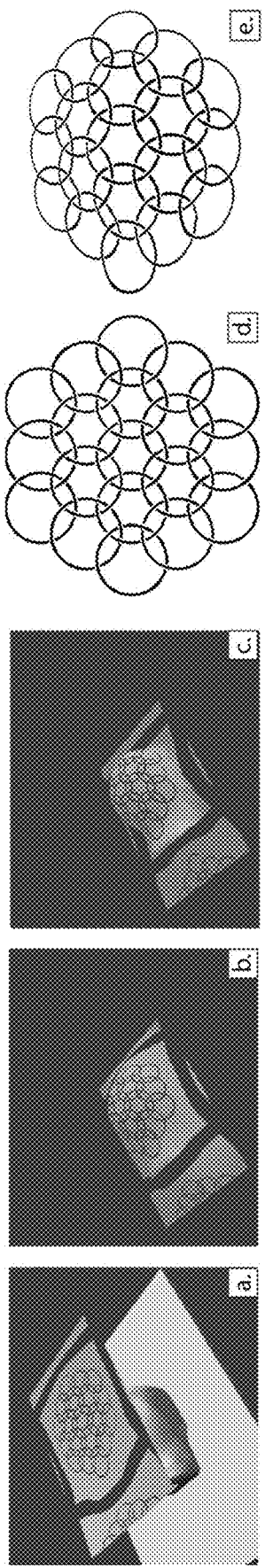
FIG. 6, panels a-e, illustrates a mechanical simulation of the forming process with a printed structure, according to an embodiment: panel a shows a resting state with pre-distorted pattern; panel b shows a model raised completely; panel c shows when a vacuum is applied, the pattern is more uniform on the 3D surface; panel d shows an undistorted input pattern; and panel e shows a pre-distorted output pattern.

Vacuum forming inherently causes a change, oftentimes large, in surface area. This may distort printed geometries thereby changing coil overlaps and inductances. FIG. 6, panels a-e, illustrate a simulation of the forming process with a printed structure. With simulation, the printed structures can be pre-distorted to yield evenly spaced coils on the 3D surface.

In an embodiment, a graphical simulation is used to combat the deformation inherent to the vacuum forming process. A plastic sheet may be modeled as a system of masses and springs. The sheet is lowered over the mold with a constant velocity until it touches the platform. Collisions are handled with the Embree Ray Tracing Kernel. Vacuum force is applied as shown in FIG. 6. The resultant mesh is then parameterized with the As Rigid As Possible (ARAP) conformal mapping method from the open source Computational Geometry Algorithms Library (CGAL). This provides a mapping from the 3D mesh to a 2D graph with minimal area and angular distortion. With this mapping, the input image of an undistorted coil array (FIG. 6, panel d) can be converted to an image which will produce uniformly patterned coils after vacuum forming (FIG. 6, panel e).

Figure 7:
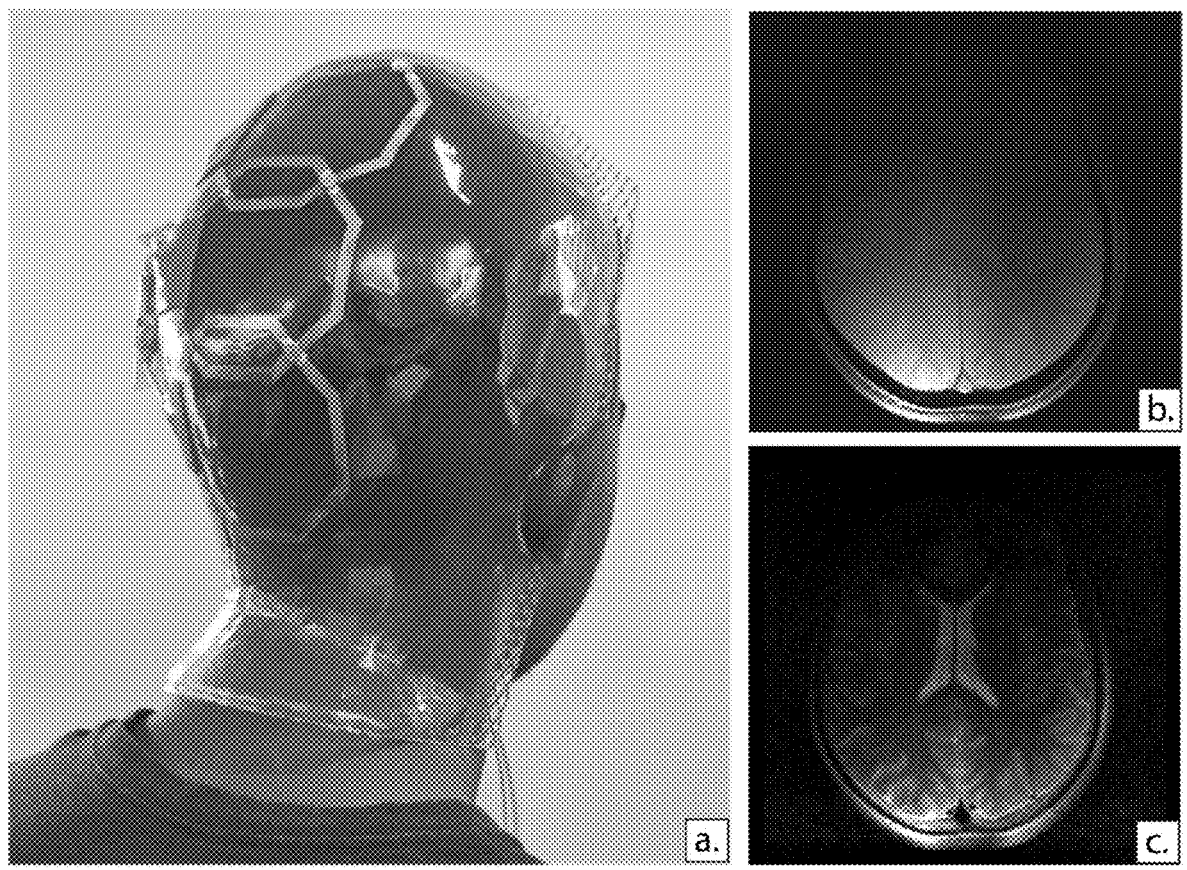
FIG. 7 illustrates in panels a-c an example embodiment of a coil device placed on a volunteer.

FIG. 7, panel a, illustrates an example embodiment of a coil device placed on a volunteer. The device includes a receive array made of 3 octagonal, 8 cm diameter elements constructed with the methods described herein. Each coil was tuned and matched to a center frequency of 123.3 MHz. All coils exhibited return losses of less than −30 dB. The unloaded Q of each coil was around 40. This is likely due to oxidization of the thin copper surfaces and the use of variable capacitors. It is expected that the Q will increase with extended copper plating times.

Test sequences were performed on a watermelon to verify coil decoupling and ensure safe operation. Afterwards, the coil was attached to the back of the volunteer's head. Gradient echo (FIG. 7, panel b: GRE-TE: 10, TR: 438) and turbo spin echo (FIG. 7, panel c: TSE-TE: 112, TR: 3490) sequences with 0.6×0.6 mm resolution and 5 mm slice thickness were performed on a volunteer in a Siemens 3T Trio scanner. The scans reveal high SNR near the coil elements. This demonstrates potential for moving to higher channel counts spaced evenly around the region of interest.

In certain embodiments, the substrates used in embodiments may include a thin, flexible material, such as a film. The substrate films are preferably flexible, but may include rigid or semi-rigid materials. Examples of useful substrate materials include PET (Polyethylene terephthalate), Kapton (polyimide), PEN (Polyethlye napthaline), PEEK (Polyether ether ketone), PI (polyimide), PEI (polyetherimide), PTFE (polytetrafluoroethylene), PAEK (polyaryletherketone), (PES) Polyethersulphone, other polymermaterials, and other flexible or non-flexible materials. Prior to printing, the substrate may be preheated to the temperature seen during annealing to relieve any stress and prevent distortion in future processing steps. The substrate may then be allowed to cool to room temperature before proceeding onto the printing process.

The MRI receive coil devices herein create a higher Signal-to-Noise Ratio (SNR) on more body types and physiologies than traditional inflexible coils because of their ability to intimately conform to many types of physiologies.

In certain embodiments, printed flexible receive coils arrays for MRI scanners are fabricated using additive solution processing techniques to print (form) conductors, insulators, capacitors, inductors, transmission lines and other discrete elements needed for proper device function.

In one embodiment, screen printing is used to print the coil arrays. This takes advantage of the benefits of high throughput, thick films for good conductivity, large area of coverage, and low cost screen printing offers compared to traditional fabrication techniques. Other printing techniques may be used, e.g., roto-gravure, stamp, flexographic, etc. techniques In certain embodiments, an entire MRI receive coil device may be thin (e.g., less than 1.0 mm or less than 0.1 mm) allowing for a new level of conforming to the patient. Coils according to various embodiments can be tuned for human scanning systems, e.g., specifically 1.5T, 3T, but can easily be adapted for 7T or other possible systems.

Reference is made to U.S. Pat. No. 9,696,393, which is incorporated by reference in its entirety, for additional and supplemental information regarding MRI receive coils, fabrication processes and materials.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the embodiments (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosed embodiments and does not pose a limitation on the scope of the disclosure unless otherwise claimed. No language in the specification should be construed as indicating any non-claimed element as essential to the practice of the embodiments.

Exemplary embodiments are described herein. Variations of those exemplary embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, the scope of the disclosure includes all modifications and equivalents of the subject matter recited herein and in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A method of making a shape-conforming magnetic resonance imaging (MRI) receive coil device, the method comprising:
    a) providing a 3-dimensional (3D) mold structure matching a curvilinear shape of interest; and
    b) forming a receive coil pattern on an outer surface of the 3D mold structure, wherein the forming a receive coil pattern includes spraying and/or depositing a conductive material and a dielectric material on at least a portion of the outer surface of the 3D mold structure to form the receive coil pattern.

2. The method of claim 1, wherein the 3D mold structure comprises an MRI-transparent material and has an inner surface that matches the shape of interest.

3. The method of claim 2, wherein the MRI-transparent material includes a cyanide ester resin.

4. The method of claim 1, wherein the conductive and dielectric materials include solution processed electronic materials.

5. The method of claim 1, wherein the conductive material includes a solution processed metal material and the dielectric material includes solution processed polystyrene.

6. The method of claim 5, wherein the solution processed metal material comprises a silver ink.

7. A flexible magnetic resonance imaging (MRI) receive coil device formed according to the method of claim 1.

8. The method of claim 1, wherein the providing a 3D mold structure includes 3D printing the 3D mold structure.

9. The method of claim 1, wherein the providing a 3D mold structure includes scanning a portion or body part of a patient and creating a 3D mold structure of the portion or body part of the patient, wherein the portion or body part of the patient corresponds to the curvilinear shape of interest.

10. A method of making a shape-conforming magnetic resonance imaging (MRI) receive coil device, the method comprising:
    a) providing a 3-dimensional (3D) mold structure matching a curvilinear shape of interest; and
    b) forming a receive coil pattern on an outer surface of the 3D mold structure, wherein the forming a receive coil pattern includes:
    providing a flat substrate sheet;
    forming the receive coil pattern on an outer surface of the flat substrate sheet; and
    vacuum forming an inner surface of the flat substrate sheet to the outer surface of the 3D mold structure to form a shape-conforming substrate sheet.

11. The method of claim 10, further comprising, removing the shape-conforming substrate sheet from the 3D mold structure.

12. The method of claim 10, wherein the receive coil pattern formed on the outer surface of the flat substrate sheet is pre-distorted according to the curvilinear shape of interest, such that when formed the shape-conforming substrate sheet includes uniformly patterned coils.

13. The method of claim 10, wherein the providing a 3D mold structure includes 3D printing the 3D mold structure.

14. The method of claim 10, wherein the forming the receive coil pattern includes spraying and/or depositing a conductive material and a dielectric material on at least a portion of the outer surface of the flat substrate sheet to form the receive coil pattern.

15. The method of claim 10, wherein the providing a 3D mold structure includes scanning a portion or body part of a patient and creating a 3D mold structure of the portion or body part of the patient, wherein the portion or body part of the patient corresponds to the curvilinear shape of interest.

16. The method of claim 10, wherein the forming the receive coil pattern includes electroless plating of conductive traces in the receive coil pattern.

17. A flexible magnetic resonance imaging (MRI) receive coil device formed according to the method of claim 10.

18. A method of making a shape-conforming magnetic resonance imaging (MRI) receive coil device, the method comprising:
    a) providing a 3-dimensional (3D) mold structure matching a curvilinear shape of interest; and b) forming a receive coil pattern on an outer surface of the 3D mold structure, wherein the providing a 3D mold structure includes scanning a portion or body part of a patient and creating a 3D mold structure of the portion or body part of the patient, wherein the portion or body part of the patient corresponds to the curvilinear shape of interest.

19. The method of claim 18, wherein the creating a 3D mold structure includes 3D printing the 3D mold structure.

20. The method of claim 18, wherein the forming the receive coil pattern includes spraying and/or depositing a conductive material and a dielectric material on at least a portion of the outer surface of the 3D mold structure to form the receive coil pattern.

* * * * *